United States Patent [19]

Sugimura et al.

[11] Patent Number: 4,740,507
[45] Date of Patent: Apr. 26, 1988

[54] CARBAPENEM COMPOUNDS AND USE

[75] Inventors: Yukio Sugimura; Toshihiko Hashimoto; Teruo Tanaka; Kimio Iino; Tomoyuki Shibata; Tetsuo Miyadera; Shinichi Sugawara, all of Hiromachi, Japan

[73] Assignee: Sankyo Company Limited, Tokyo, Japan

[21] Appl. No.: 812,344

[22] Filed: Dec. 23, 1985

[30] Foreign Application Priority Data

Dec. 25, 1984 [JP] Japan .................. 59-281700

[51] Int. Cl.$^4$ .................. C07D 487/04; A61K 31/40
[52] U.S. Cl. .................. 514/210; 540/350
[58] Field of Search .................. 260/245.2 T; 514/210; 540/350

[56] References Cited

U.S. PATENT DOCUMENTS 4,383,946  5/1983  Christenson et al. ......... 260/245.2 T
4,552,873  11/1985  Muyadera et al. .............. 514/210

FOREIGN PATENT DOCUMENTS 0126587  11/1984  European Pat. Off. .

Primary Examiner—Nicholas S. Rizzo
Attorney, Agent, or Firm—Frishauf, Holtz, Goodman, Woodward

[57] ABSTRACT

Compounds of formula (I):

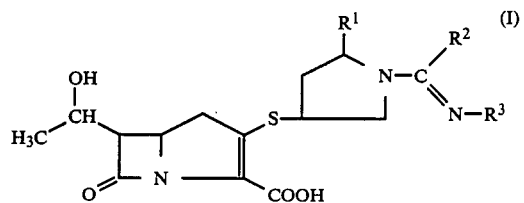

(wherein $R^1$ is carboxy, $-CONR^4R^5$, cyano or hydroxymethyl, and $R^2$ and $R^3$ are hydrogen, alkyl or substituted alkyl, $R^4$ and $R^5$ being hydrogen or a variety of groups) have good antibiotic activity and reduced renal toxicity.

5 Claims, No Drawings

CARBAPENEM COMPOUNDS AND USE

BACKGROUND OF THE INVENTION

The present invention relates to series of novel carbapenem compounds, and provides a process for preparing them and compositions containing them.

The carbapenem compounds have recently been developed as a potentially valuable series of antibiotics, and a variety of carbapenem compounds have been proposed for such use. The carbapenems are based upon the carbapenem nucleus, which may be represented by the following formula:

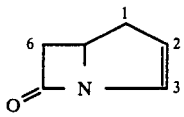

Shown on the above formula is the numbering system commonly applied to such compounds. It can be seen that the carbapenems are structural analogs of the penicillins, in which the sulfur atom at the 1-position of the basic penicillin nucleus has been replaced by a carbon atom. The majority of carbapenem compounds have a carboxy group or a conventional derivative thereof (e.g. ester, salt or amide group) at the 3-position.

The present invention provides a limited class of compounds having, at their 2-positions, a particular selection of 1,2-disubstituted-4-pyrrolidinylthio groups.

Certain compounds similar to this are known. For example, Japanese Patent Application Kokai (i.e. laid upon to public inspection) No. 59-16892 discloses a group of compounds having, inter alia, a 1-hydroxyethyl group at the 6-position and, inter alia, a wide range of substituted pyrrolidinylthio groups at the 2-position. Likewise, European Patent Publication No. 126,587 discloses a class of penem compounds and their carbapenem analogs having, inter alia, a 1-hydroxyethyl group at the 6-position and a wide selection of substituted 4-pyrrolidinylthio groups at the 2-position. For example, amongst the compounds specifically disclosed in this European Patent Publication are the compounds 6-(1-hydroxyethyl)-2-(2-dimethylcarbamoyl-4-pyrrolidinylthio)-2-carbapenem-3-carboxylic acid and 6-(1-hydroxyethyl)-2-(2-carbamoyl-4-pyrrolidinylthio)-2-carbapenem-3-carboxylic acid.

In U.S. patent application Ser. No. 714,373 filed 21 Mar. 1985, there is disclosed a class of carbapenem derivatives, some of which are similar to those of the present invention, but distinguished in that the prior compounds are characterized by the presence of at least one, and optionally two, substituents at the 1-carbapenem site.

We have now surprisingly found that a specific class of 6-(1-hydroxyethyl)-2-(1,2-disubstituted-4-pyrrolidinylthio)-2-carbapenem-3-carboxylic acid derivatives in which the substituents at the 2-position of the pyrrolidinyl ring are chosen from a limited class of carboxy, carbamoyl, cyano and hydroxymethyl and related groups and in which the same compound also has at the 1-position of the pyrrolidinyl ring a limited class of imidoyl substituents combines both reduced renal toxicity and excellent bioavailability. Since undesirably high renal toxicity and limited bioavailability are two common disadvantages of the carbapenem group of compounds, these advantages of the compounds of the invention are expected to lead to exciting therapeutic possibilities.

BRIEF SUMMARY OF INVENTION

It is, therefore, an object of the invention to provide a class of carbapenem compounds having reduced renal toxicity and enhanced bioavailability as compared with conventional such compounds.

It is a further object of the invention to provide a process for preparing such compounds.

It is a still further object of the invention to provide a method of treatment of bacterial infections employing such compounds.

The compounds of the present invention are those compounds of formula (I):

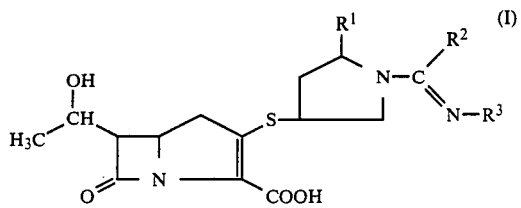

in which:
$R^1$ represents a carboxy group, a group of formula $-CONR^4R^5$, in which:
  $R^4$ represents a hydrogen atom or a $C_1-C_4$ alkyl group; and
  $R^5$ represents a hydrogen atom, a $C_1-C_4$ alkyl group, a $C_2$ or $C_3$ alkenyl group, a $C_2$ or $C_3$ alkynyl group, a $C_3-C_6$ cycloalkyl group, a phenyl group, a hydroxy group, a $C_1-C_4$ alkoxy group, a cyano group or a substituted $C_1-C_4$ alkyl group having at least one substituent selected from the group consisting of phenyl, carbamoyl, cyano and carboxy substituents, or $R^4$ and $R^5$ together form a $C_2-C_5$ alkylene group or an alkyleneoxyalkylene group in which each alkylene part is $C_1-C_3$;
a cyano group or a hydroxymethyl group;
$R^2$ represents a hydrogen atom, a $C_1-C_4$ alkyl group, an alkoxyalkyl group in which the alkoxy and alkyl parts are both $C_1-C_4$, a cyanoalkyl group in which the alkyl part is $C_1-C_4$, a $C_1-C_4$ alkyl group having at least one halogen substituent, or an alkylthioalkyl group in which both alkyl parts are independently selected from the group consisting of $C_1-C_4$ alkyl groups; and
$R^3$ represents a hydrogen atom or a $C_1-C_4$ alkyl group;
and pharmaceutically acceptable salts and esters thereof.

The invention also provides a method of treating bacterial infections in a mammal, which may be human or non-human, which comprises administering to said mammal an effective amount of an antibiotic, wherein the antibiotic is selected from the group consisting of compounds of formula (I), and salts and esters thereof.

The invention still further consists in a pharmaceutical composition for the treatment of bacterial infections, comprising an active compound in admixture with a pharmaceutically acceptable carrier or diluent, wherein the active compound is selected from the group consisting of compounds of formula (I) and pharmaceutically acceptable salts and esters thereof.

The compounds of the present invention may be prepared by:

(a) reacting a compound of formula (III):

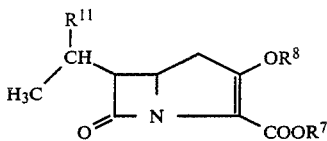

(in which $R^7$ represents a carboxy-protecting group, $R^8$ represents an alkanesulfonyl group, an arylsulfonyl group, a dialkylphosphoryl group or a diarylphosphoryl group and $R^{11}$ represents a hydroxy group or a protected hydroxy group) or a ring-opened azetidinone analog thereof with a compound of formula (IV):

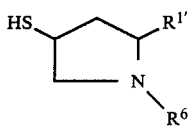

[in which $R^{1'}$ represents any one of the groups represented by $R^1$ or any one of said groups represented by $R^1$ in which any reactive group or atom is protected, and $R^6$ represents a hydrogen atom or a group of formula $-C(R^2)=NR^3$, in which $R^2$ and $R^3$ are as defined above], to give a compound of formula (V):

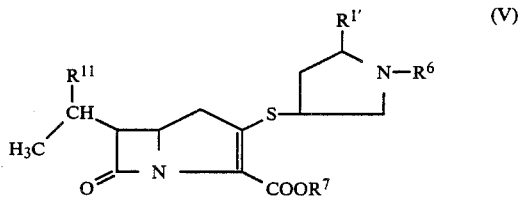

(in which $R^{1'}$, $R^6$, $R^7$ and $R^{11}$ are as defined above) or a ring-opened azetidinone analog thereof;

(b) where $R^6$ represents a hydrogen atom, reacting said compound of formula (V) with a compound of formula (VI):

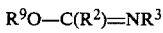

$$R^9O-C(R^2)=NR^3 \quad (VI)$$

(in which $R^2$ and $R^3$ are as defined above and $R^9$ represents a hydrogen atom or a $C_1-C_4$ alkyl group) or with a reactive derivative thereof, to give a compound of formula (Va):

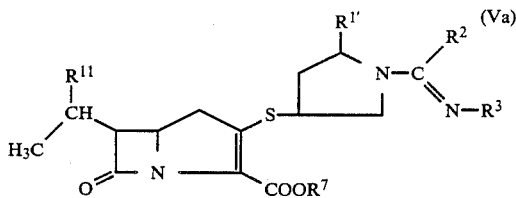

(in which $R^{1'}$, $R^2$, $R^3$, $R^7$ and $R^{11}$ are as defined above) or a ring-opened azetidinone analog thereof;

(c) if necessary, at any appropriate stage removing protecting groups and subjecting any ring-opened azetidinone analog to a ring-closing Wittig reaction; and (d) optionally salifying and/or esterifying the compound.

DETAILED DESCRIPTION OF INVENTION

The compounds of formula (I) necessarily contain at least one carboxy group—the carboxy group shown at the 3-position of the carbapenem system—but can additionally contain another carboxy group, if $R^1$ represents a carboxy group or if $R^1$ represents a group of formula $-CONR^4R^5$, in which $R^5$ represents an alkyl group having at least one carboxy substituent. These carboxy groups are, of course, acidic groups and can, therefore, form salts and esters. In principle, there is no limitation on the nature of the salts and esters which can be formed by the compounds of the present invention and any salt or ester known for use in the field of β-lactam antibiotics may be employed. The only restriction is that, where the compounds of the invention are to be used for therapeutic purposes, the resulting salt or ester must be pharmaceutically acceptable which, as is well-known to those skilled in the art, means that the salt or ester must not have an increased, or substantially increased, toxicity or a reduced, or substantially reduced, activity, as compared with the free acids of formula (I). However, where the resulting compounds are to be used for non-therapeutic purposes, for example as intermediates in the preparation of other carbapenem derivatives, even this restriction does not apply.

Of the wide range of salts which are known for this type of compound, those currently believed to be of the greatest potential interest are: metal salts, and particularly alkali metal (such as lithium, sodium or potassium) salts or alkaline earth metal (e.g. calcium or magnesium) salts; salts with basic amino acids, such as lysine or arginine; ammonium salts; and salts with organic amines (which may be primary, secondary or tertiary amines) or quaternary ammonium salts, particularly the cyclohexlammonium, diisopropylammonium and triethylammonium salts. Of these, the sodium and potassium salts are preferred.

The range of potential esters known to those skilled in the art in this field is even wider and it would serve no useful purpose to repeat all possible esters here. However, those esters currently believed to be of the greatest potential interest include:

$C_1-C_6$ alkyl esters, in which the alkyl group is a straight or branched chain $C_1-C_6$, preferably $C_2-C_4$, alkyl group, for example the methyl, ethyl, propyl, isopropyl, butyl, isobutyl or t-butyl esters;

$C_1-C_4$, preferably $C_1-C_2$, halogenated alkyl esters, such as the 2-iodoethyl, 2-chloroethyl, 2-bromoethyl, 2,2-dibromoethyl or 2,2,2-trichloroethyl esters;

alkoxymethyl esters in which the alkoxy part is $C_1-C_6$, preferably $C_1-C_4$, and may be a straight or branched chain group, for example the methoxymethyl, ethoxymethyl, propoxymethyl, isopropoxymethyl, butoxymethyl and isobutoxymethyl esters;

aliphatic carboxylic acyloxymethyl esters in which the aliphatic carboxylic acyl group is a $C_1-C_7$, preferably $C_2-C_5$, acyl group and is more preferably a $C_1-C_7$, preferably $C_2-C_5$, alkanoyl group, for example the acetoxymethyl, propionyloxymethyl, butyryloxymethyl, isobutyryloxymethyl or pivaloyloxymethyl esters;

1-alkoxycarbonyloxyethyl esters, in which the alkoxy part is a $C_1-C_6$, preferably $C_1-C_4$, alkoxy group which may be a straight or branched chain group, for example the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl or 1-isobutoxycarbonyloxyethyl esters;

$C_7$–$C_9$ aralkyl esters in which the aryl part is unsubstituted or has at least one (and possibly from 1 to 5, preferably from 1 to 3 and more preferably 1) substituent selected from the group consisting of $C_1$–$C_4$ alkyl groups (e.g. those exemplified above in relation to alkyl esters), $C_1$–$C_4$ alkoxy groups (e.g. those exemplified above as part of the alkoxymethyl esters), halogen atoms (e.g. fluorine, chlorine, bromine or iodine atoms), hydroxy groups, nitro groups, cyano groups, carboxy groups or carbamoyl groups, for example the benzyl, phenethyl, 2-phenylpropyl, 3-phenylpropyl, 4-methoxybenzyl, 2-nitrobenzyl or 4-nitrobenzyl esters;

the benzhydryl esters;

the (5-methyl-2-oxo-1,3-dioxolen-4-yl)methyl esters; and the phthalidyl esters.

Although any of the above esters, or any other conventional ester, may be formed with any of the carboxy groups in the compounds of formula (I), in practice, where $R^1$ represents a carboxy group or represents a group of formula —$CONR^4R^5$ and $R^5$ represents an alkyl group having a carboxy substituent, preferred esters of these carboxy groups are the $C_1$–$C_4$ alkyl esters, and particularly those exemplified above, i.e., in those cases, $R^1$ represents a $C_2$–$C_5$ alkoxycarbonyl group or a group of formula —$CONR^4R^5$ in which $R^5$ represents a $C_1$–$C_4$ alkyl group having at least one $C_2$–$C_5$ alkoxycarbonyl substituent.

In the case of the carboxy group at the 3-position of the carbapenem nucleus, this preferably forms any one of the above esters, e.g. the alkyl, haloalkyl, alkoxymethyl, acyloxymethyl, alkoxycarbonyloxyethyl, aralkyl, benzhydryl, (5-methyl-2-oxo-1,3-dioxolen-4-yl)methyl or phthalidyl esters.

Where $R^1$ represents a hydroxymethyl group, the resulting compound can also form esters but, in this case, the hydroxymethyl group acts as an alcoholic group and thus the compound can form esters with acids. As in the case of the salts and esters discussed above, there is no particular restriction on the nature of the acid employed, except that, where the compounds are to be used for the therapeutic purposes, the resulting esters must be pharmaceutically acceptable, and any acid commonly known for use in the formation of esters in the field of β-lactam antibiotics may be employed. Amongst the many such acids, those currently believed to be of greatest potential interest include: the $C_1$–$C_7$ aliphatic carboxylic acids, and particularly the $C_2$–$C_5$ aliphatic carboxylic, and more preferably alkanoic, acids, such as acetic acid, propionic acid, butyric acid, isobutyric acid, pivalic acid, valeric acid and isovaleric acid; carbamic acid and the N-alkyl and N,N-dialkyl analogs thereof; benzoic acid, in which the benzene ring is unsubstituted or has one or more substituents selected from the substituents given above in relation to substituents on aralkyl groups; and cinnamic acid. Of these, the preferred acids are the $C_2$–$C_5$ alkanoic acids and carbamic acid, i.e. $R^1$ preferably represents a ($C_2$–$C_5$ alkanoyl)oxymethyl or carbamoyloxymethyl group.

The nitrogen atom in the imidoyl group at the 1-pyrrolidinyl site is basic in character and can, therefore, form acid addition salts. As with the salts and esters discussed above, the nature of the acid employed is not critical, except that, where the resulting salt is to be employed for therapeutic purposes, it must be pharmaceutically acceptable. Examples of suitable acids include: inorganic acids, such as hydrochloric acid, sulfuric acid and phosphoric acid; organic carboxylic acids, such as acetic acid, citric acid, tartaric acid, malonic acid, maleic acid, malic acid, itaconic acid, citraconic acid and succinic acid; and organic sulfonic acids, such as methanesulfonic acid, benzenesulfonic acid, naphthalenesulfonic acid and p-toluenesulfonic acid.

In the compounds of the invention, where $R^4$, $R^5$, $R^2$ or $R^3$ represents a $C_1$–$C_4$ alkyl group, this may be a straight or branched chain group and examples include the methyl, ethyl, propyl, isopropyl, butyl, isobutyl, sec-butyl and t-butyl groups.

Where $R^5$ represents a $C_2$ or $C_3$ alkenyl or alkynyl group, this may be a vinyl, 1-propenyl, allyl, ethynyl, 1-propynyl or 2-propynyl group.

Where $R^5$ represents a $C_3$–$C_6$ cycloalkyl group, this may be a cyclopropyl, cyclobutyl, cyclopentyl or cyclohexyl group.

Where $R^5$ represents a $C_1$–$C_4$ alkoxy group, this may be a straight or branched chain group and examples include the methoxy, ethoxy, propoxy, isopropoxy, butoxy, isobutoxy, sec-butoxy and t-butoxy groups.

Where $R^5$ represents a substituted $C_1$–$C_4$ alkyl group, this has at least one, and preferably only one, substituent selected from the group consisting of phenyl, carbamoyl, cyano and carboxy groups (and, in the case of carboxy groups, these may, as described above, be esterified). The alkyl part of the substituted alkyl group may be any one of those $C_1$–$C_4$ alkyl groups exemplified above. Examples of such substituted alkyl groups include the benzyl, phenethyl, 2-phenylpropyl, 3-phenylpropyl, carbamoylmethyl, cyanomethyl, carboxymethyl (and esterified analogs thereof), 1-carbamoylethyl, 2-carbamoylethyl, 1-cyanoethyl, 2-cyanoethyl, 1-carboxyethyl, 2-carboxyethyl (and esterified analogs of the carboxyethyl groups), 3-carbamoylpropyl, 3-cyanopropyl, 3-carboxypropyl (and esterified analogs thereof), 4-carbamoylbutyl, 4-cyanobutyl and 4-carboxybutyl (and esterified analogs thereof) groups.

Where $R^4$ and $R^5$ together represent a $C_2$–$C_5$ alkylene group or an alkyleneoxyalkylene group (in which each alkylene part is $C_1$–$C_3$, preferably together totalling $C_3$ or $C_4$ and more preferably each is $C_2$), then the group —$NR^4R^5$ is a nitrogen-containing saturated heterocyclic group. Examples of such groups represented by $R^4$ and $R^5$ are the ethylene, trimethylene, tetramethylene, pentamethylene, methyleneoxyethylene and ethyleneoxyethylene groups and examples of the heterocyclic groups represented by —$NR^4R^5$ are the 1-aziridinyl, 1-azetidinyl, 1-pyrrolidinyl, piperidino, perhydro-1,3-oxazol-3-yl and morpholino groups, of which the 1-aziridinyl, piperidino and morpholino, especially piperidino and morpholino, groups are preferred.

Where $R^2$ represents an alkoxyalkyl group, the alkoxy and alkyl parts are both $C_1$–$C_4$ groups, which may be straight or branched groups, and examples include the alkoxy and alkyl groups exemplified above. Preferred such alkoxyalkyl groups include the methoxymethyl, ethoxymethyl, propoxymethyl, butoxymethyl, 2-methoxyethyl, 2-ethoxyethyl, 2-propoxyethyl, 3-methoxypropyl, 3-ethoxypropyl, 3-propoxypropyl, 4-methoxybutyl, 4-ethoxybutyl and 4-propoxybutyl groups.

Where $R^2$ represents a cyanoalkyl group, the alkyl part is a $C_1$–$C_4$ alkyl group, which may be a straight or branched chain group and examples include the alkyl groups exemplified above. Examples of such cyanoalkyl groups include the cyanomethyl, 2-cyanoethyl, 3-cyanopropyl and 4-cyanobutyl groups.

Where $R^2$ represents a $C_1$–$C_4$ alkyl group having at least one halogen substituted, the alkyl part may be any one of the $C_1$–$C_4$ alkyl groups, straight or branched-chain, exemplified above, and the halogen atom is preferably fluorine, chlorine, bromine or iodine. Example of such haloalkyl groups include the fluoromethyl, chloromethyl, dichloromethyl, trifluoromethyl, 2-iodoethyl, 2-chloroethyl, 2-bromoethyl, 2-fluoroethyl, 2,2-dibromoethyl, 2,2-dichloroethyl, 2,2,2-trichloroethyl, 3-chloropropyl and 4-chlorobutyl groups.

Where $R^2$ represents an alkylthioalkyl group, each alkyl part is a $C_1$–$C_4$ alkyl group, which may be straight or branched-chain, and examples are as given above. Preferred alkylthioalkyl groups include the methylthiomethyl, 2-methylthioethyl, 3-methylthiopropyl, 4-methylthiobutyl, ethylthiomethyl and 2-ethylthioethyl groups.

Of the compounds of the invention, we particularly prefer those compounds in which $R^1$ represents a group of formula —$CONR^4R^5$, in which $R^4$ represents a hydrogen atom or a methyl group and $R^5$ represents a hydrogen atom, a methyl group, a hydroxy group or a methoxy group. More preferred are such compounds in which $R^4$ represents a hydrogen atom and most preferred are such compounds in which $R^5$ also represents a hydrogen atom.

We also particularly prefer compounds in which $R^2$ represents a hydrogen atom, a methyl group, an ethyl group, a methoxymethyl group, a methylthiomethyl group, a cyanomethyl group or a halomethyl group.

$R^3$ is preferably a hydrogen atom.

A preferred class of compounds are those compounds of formula (I) in which:

$R^1$ represents an alkoxycarbonyl group in which the alkoxy part is $C_1$–$C_4$ or a group of formula —$CONR^4R^5$ in which $R^4$ represents a hydrogen atom or a methyl group and $R^5$ represents a hydrogen atom, a methyl group, a hydroxy group or a methoxy group;

$R^2$ represents a hydrogen atom, a methyl group, an ethyl group, a methoxymethyl group, a methylthiomethyl group, cyanomethyl group or a halomethyl group; and $R^3$ represents a hydrogen atom.

Of these, a more preferred class of compounds are those in which $R^1$ represents a group of formula —$CONR^4R^5$ in which $R^4$ represents a hydrogen atom and $R^5$ represents a hydrogen atom, a methyl group, a hydroxy group or a methoxy group, more preferably a hydrogen atom.

The compounds of the present invention can exist in the form of various optical isomers and stereoisomers, due to the presence of asymmetric carbon atoms. Although all of these isomers are represented herein by a single formula, it should be understood that the present invention envisages both the individual isolated isomers, as well as mixtures of these isomers. Preferred compounds are those in which the carbon atom at the 5-position is in the same configuration as in the known compound thienamycin, that is to say the R-configuration. In particular, we prefer compounds having the (5R,6S) or (5R,6R) configuration. We also particularly prefer that the carbon atom at the 1-position of the 6-(1-hydroxyethyl) substituent should also adopt the R-configuration.

Examples of preferred compounds of the invention are given in the following list and the compounds are hereafter, where appropriate, referred to by the numbers assigned to them in this list. In this list, the configuration of asymmetric carbon atoms is not specified and each of the compounds given in this list may be a single isomer adopting any of the possible configurations or may be a mixture of isomers. However, the listed compounds are preferably (5R,6R) or (5R,6R) and more preferably the 6-substituent is 6-[1(R)-hydroxyethyl].

In the following list, the following abbreviations are used:

| | |
|---|---|
| Azi | 1-aziridinyl |
| cHx | cyclohexyl |
| Mor | morpholino |
| Ph | phenyl |
| Pip | piperidino |

| Cpd No | $R^1$ | $R^2$ | $R^3$ |
|---|---|---|---|
| 1 | $CONH_2$ | H | H |
| 2 | $CONH_2$ | $CH_3$ | H |
| 3 | $CONH_2$ | H | $CH_3$ |
| 4 | $CONH_2$ | $CH_3$ | $CH_3$ |
| 5 | $CONH_2$ | $C_2H_5$ | H |
| 6 | $CONH_2$ | n-$C_3H_7$ | H |
| 7 | $CONH_2$ | $CH_2OCH_3$ | H |
| 8 | $CONH_2$ | $CH_2SCH_3$ | H |
| 9 | $CONH_2$ | $CH_2CN$ | H |
| 10 | $CONH_2$ | $CH_2Cl$ | H |
| 11 | $CONH_2$ | $CH_2F$ | H |
| 12 | —$CONHCH_3$ | H | H |
| 13 | —$CONHCH_3$ | $CH_3$ | H |
| 14 | —$CONHCH_3$ | $CH_3$ | $CH_3$ |
| 15 | —$CON(CH_3)_2$ | H | H |
| 16 | —$CON(CH_3)_2$ | $CH_3$ | H |
| 17 | —$CONHC_2H_5$ | H | $CH_3$ |
| 18 | —$CONHC_2H_5$ | $CH_3$ | H |
| 19 | —$CONHCO_2C_2H_5$ | H | H |
| 20 | —$CONHCO_2C_2H_5$ | $CH_3$ | H |
| 21 | —$CONHCH_2CN$ | H | H |
| 22 | —$CONHCH_2CN$ | $CH_3$ | H |
| 23 | —$CONHCH_2CONH_2$ | H | H |
| 24 | —$COHNCH_2CONH_2$ | $CH_3$ | H |
| 25 | —CONH—cHx | H | H |
| 26 | —CONH—cHx | $CH_3$ | H |
| 27 | —CONH—Ph | H | H |
| 28 | —CONH—Ph | $CH_3$ | H |
| 29 | —$CONHCH_2CH=CH_2$ | $CH_3$ | H |
| 30 | —$CONHCH_2C\equiv CH$ | $CH_3$ | H |
| 31 | $CONHCH_2$—Ph | $CH_3$ | H |
| 32 | $CONHOCH_3$ | H | H |
| 33 | $CONHOCH_3$ | $CH_3$ | H |
| 34 | CONHOH | $CH_3$ | H |
| 35 | CONHCN | $CH_3$ | H |
| 36 | —CO—Azi | H | H |
| 37 | —CO—Azi | $CH_3$ | H |
| 38 | —CO—Pip | H | H |
| 39 | —CO—Pip | $CH_3$ | H |
| 40 | —CO—Mor | H | H |
| 41 | —CO—Mor | $CH_3$ | H |
| 42 | —CN | $CH_3$ | H |
| 43 | —$COOCH_3$ | H | H |
| 44 | —$COOCH_3$ | $CH_3$ | H |
| 45 | —$COOC_2H_5$ | $CH_3$ | H |
| 46 | —$CH_2OH$ | $CH_3$ | H |
| 47 | —$CH_2OCOCH_3$ | H | H |
| 48 | —$CH_2OCOCH_3$ | $CH_3$ | H |
| 49 | —$CH_2OCONH_2$ | $CH_3$ | H |

Of the compounds listed above, the preferred compounds are Compounds No. 2, 7, 13, 16, 33, 34, 44, 46, 48 and 49, and especially the 6-[1(R)-hydroxyethyl]-(5R,6S) isomers thereof, i.e.:

2. (5R,6S)-6-[1(R)-hydroxyethyl]-2-(2-carbamoyl-1-acetimidoylpyrrolidin-4-ylthio)-2-carbapenem-3-carboxylic acid 7. (5R,6S)-6-[1-(R)-hydroxyethyl]-2-[2-carbamoyl-1-(α-methoxyacetimidoyl)pyrrolidin-4-ylthio]-2carbapenem-3-carboxylic acid 13. (5R,6S)-6-[1(R)-hydroxyethyl]-2-(2-N-methylcarbamoyl-1-acetimidoylpyrrolidin-4-ylthio)-2-carbapenem-3-carboxylic acid 16. (5R,6S)-6-[1(R)-hydroxyethyl]-2-(2-N,N-dimethylcarbamoyl-1-acetimidoylpyrrolidin-4-ylthio)-2-carbapenem-3-carboxylic acid 33. (5R,6S)-6-[1(R)-hydroxyethyl]-2-(2-N-methoxycarbamoyl-1-acetimidoylpyrrolidin-4-ylthio)-2-carbapenem-3-carboxylic acid 34. (5R,6S)-6-[1(R)-hydroxyethyl]-2-(2-N-hydroxycarbamoyl-1-acetimidoylpyrrolidin-4-ylthio)-2-carbapenem-3-carboxylic acid 44. (5R,6S)-6-[1(R)-hydroxyethyl]-2-(2-methoxycarbonyl-1-acetimidoylpyrrolidin-4-ylthio)-2-carbapenem-3-carboxylic acid 46. (5R,6S)-6-[1-(R)-hydroxyethyl]-2-(2-hydroxymethyl-1-acetimidoylpyrrolidin-4-ylthio)-2-carbapenem-3-carboxylic acid 48. (5R,6S)-6-[1(R)-hydroxyethyl]-2-(2-acetoxymethyl-1-acetimidoylpyrrolidin-4-ylthio)-2-carbapenem-3-carboxylic acid 49. (5R,6S)-6-[1(R)-hydroxyethyl]-2-(2-carbamoyloxymethyl-1-acetimidoylpyrrolidin-4-ylthio)-2-carbapenem-3-carboxylic acid Where any of the above compounds is hereinafter referred to by number, then it is the specific isomer listed above which is meant.

Also preferred are pharmaceutically acceptable salts and esters of the above compounds.

The compounds of the invention may be prepared by the reactions outlined in the following reaction scheme:

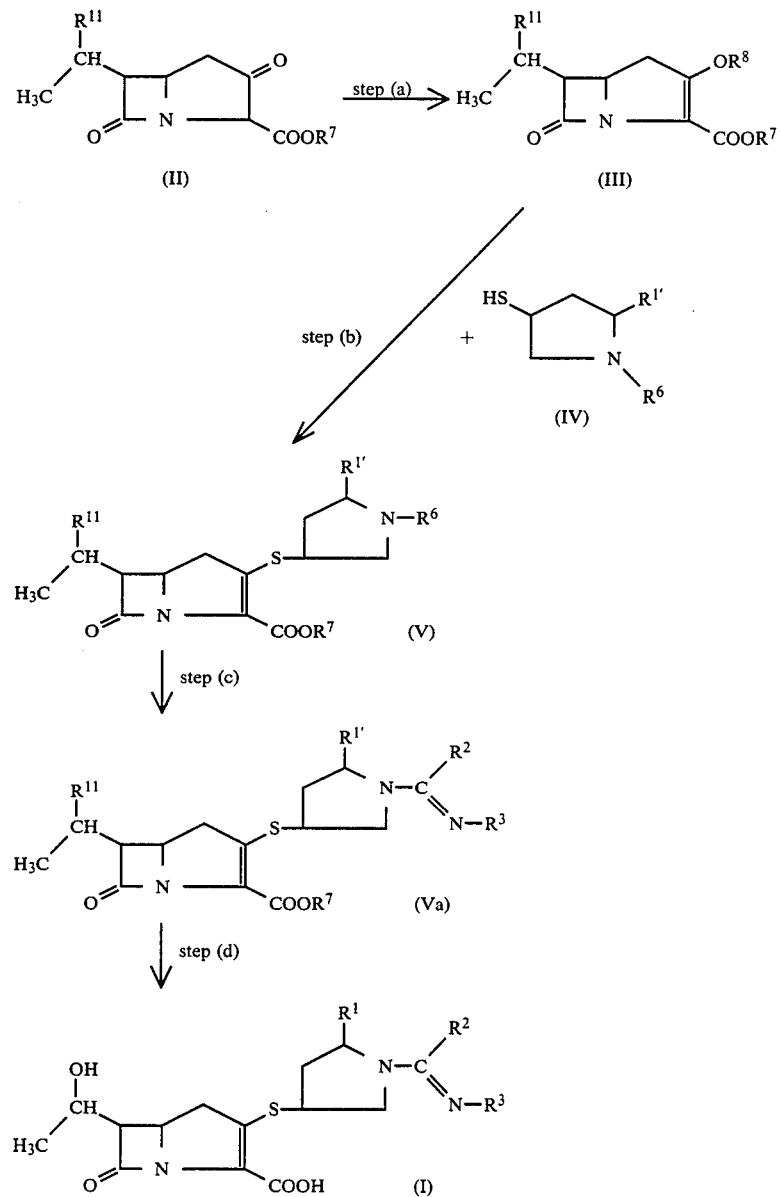

In the above formulae, $R^1$, $R^{1'}$, $R^2$, $R^3$, $R^6$, $R^7$, $R^8$ and $R^{11}$ are as define above. The reaction is carried out as follows.

Step (a)

In this step, the carbapenam-2-one compound of formula (II) is reacted with a sulfonic acid or phosphoric acid of formula $R^8OH$ (in which $R^8$ represents a sulfonyl or phosphoryl group) or with a reactive derivative (e.g. halide or anhydride) thereof, to give the compound of formula (III).

In particular, $R^8$ preferably represents a $C_1$–$C_6$ alkanesulfonyl group, an arylsulfonyl group, a dialkylphosphoryl group in which each alkyl part is $C_1$–$C_6$ or a diarylphosphoryl group in which each aryl part is a $C_6$–$C_{10}$ carbocyclic aryl group which is optionally substituted. However, the nature of the group represented by $R^8$ is of no overall significance in the process of the invention, in that this group is removed in the course of the reactions and plays no part in the final product.

Where $R^{11}$ represents a protected hydroxy group, the nature of such a group is not critical to the present invention and any such group commonly used in the field of β-lactam chemistry may be employed. Examples of such groups include acyloxy and trialkylsilyloxy groups.

Instead of using the sulfonic or phosphoric acid as such, it is possible to employ an active derivative of such a compound. Suitable active derivatives include anhydrides and halides, particularly chlorides and bromides. In particular, we prefer to employ an anhydrous alkanesulfonic acid, an anhydrous arylsulfonic acid, an alkanesulfonyl halide, an arylsulfonyl halide, a dialkylphosphoryl halide or a diarylphosphoryl halide. Preferred alkanesulfonic acids include methanesulfonic acid and ethanesulfonic acid. Preferred arylsulfonic acids include benzenesulfonic acid and p-toluenesulfonic acid. Where the alkanesulfonic and arylsulfonic acids themselves are employed, they are most preferably anhydrous. Preferred alkanesulfonyl halides include methanesulfonyl chloride and ethanesulfonyl chloride. Preferred arylsulfonyl halides include benzenesulfonyl chloride and p-toluenesulfonyl chloride. Preferred dialkylphosphoryl halides include dimethylphosphoryl chloride and diethylphosphoryl chloride. Preferred diarylphosphoryl halides include diphenylphosphoryl chloride and diphenylphosphoryl bromide. In particular, we prefer to employ anhydrous p-toluenesulfonic acid or diphenylphosphoryl chloride.

The reaction is preferably effected in the presence of a base, the nature of which is not critical, provided that it has no adverse effect on the reaction or upon the reagents, in particular the β-lactam ring. Preferred bases are organic bases, particularly triethylamine, diisopropylethylamine and 4-dimethylaminopyridine.

The reaction is preferably effected in the presence of a solvent, the nature of which is likewise not critical, provided that it has no adverse effect upon the reaction. Suitable solvents include: halogenated hydrocarbons, such as methylene chloride, 1,2-dichloroethane and chloroform; nitriles, such as acetonitrile; and amides, such as dimethylformamide or dimethylacetamide.

The reaction may be carried out over a wide range of temperatures, the reaction temperature not being critical, but we prefer to employ a relatively low temperature, in order to reduce or control side reactions. Accordingly, we prefer to employ a temperature of from $-20°$ C. to $+40°$ C. The time required for the reaction will vary, depending upon many factors, but particularly on the reaction temperature and the nature of the reagents; however, a period of from 10 minutes to 5 hours will normally suffice.

Step b

In this step, the compound of formula (III) prepared as described in step (a) is reacted with a mercaptan of formula (IV).

In the compound of formula (IV), the group represented by $R^{1'}$ may be any one of the groups represented by $R^1$ or may be any such group in which any reactive group is protected. For example, where the group $R^1$ is or contains a carboxy group, this may be protected by a carboxy-protecting group, e.g. any of those described in relation to $R^7$, and, if both carboxy groups are protected, then the two carboxy-protecting groups may be the same or different.

In the compound of formula (IV), the symbol $R^6$ may represent a hydrogen atom, a group of formula $-C(R^2)=NR^3$ or an amino-protecting group. Where $R^6$ represents the group of formula $-C(R^2)=NR^3$, the resulting compound of formula (IV) may have been prepared from the corresponding compound in which $R^6$ represents a hydrogen atom by reaction with a compound of formula (VI), $R^9O-C(R^2)=NR^3$, as described hereafter in more detail in step (c).

Where $R^6$ represents an amino-protecting group, it may be any such group capable of protecting the pyrrolidine nitrogen atom, for example an aralkyloxycarbonyl group.

This reaction, like the reaction in step (a) is preferably effected in the presence of a base, the nature of which is not critical, provided that it does not adversely affect the reaction or adversely affect the reagents, particularly the β-lactam ring. Suitable bases include: organic amines, such as triethylamine or diisopropylethylamine; and inorganic bases, particularly alkali metal carbonates, such as sodium carbonate or potassium carbonate.

The reaction temperature is not critical, but, in order to reduce or control side reactions, a relatively low temperature is preferably employed. A suitable temperature is from $-20°$ C. to ambient. The time required for the reaction will vary, depending upon many factors, but primarily upon the reaction temperature and the nature of the reagents. However, a period of from 30 minutes to 8 hours will normally suffice. This step is preferably carried out without intermediate isolation of the compound of formula (III), and hence in the same reaction medium as was employed in step (a).

Step (c)

In this step, if $R^6$ represents an amino-protecting group, this must first be removed. The reactions involved in removing such protecting groups are well-known to those skilled in the art and the details depend upon the nature of the protecting group. For example, where the protecting group is an aralkyloxycarbonyl group (e.g. a benzyloxycarbonyl or p- or o-nitrobenzyloxycarbonyl group), it may be removed by catalytic reduction using hydrogen in the presence of a suitable catalyst, such as platinum or palladium-on-charcoal, at room temperature. Such a reaction may simultaneously remove hydroxy-protecting groups and/or carboxy-protecting groups, depending upon their nature. The deprotected compound is then reacted, normally without isolation from the reaction mixture, with the compound of formula (VI):

$$R^9O-C(R^2)=NR^3 \qquad \text{(VI)}$$

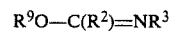

In this formula, $R^2$ and $R^3$ are as defined above and $R^9$ represents a hydrogen atom or a $C_1$–$C_4$ alkyl group. Examples of such alkyl groups are as given herein in relation to the similar groups which may be represented by $R^2$–$R^5$.

The reaction is preferably effected in an aqueous medium, more preferably in a phosphate buffer solution maintained at a slightly alkaline pH value, e.g. a value of around 8. The reaction will take place over a wide range of temperatures, e.g. from $-10°$ C. to $+50°$ C., more preferably from $0°$ C. to ambient temperature. The time required for the reaction will vary, depending upon many factors, including the reaction temperature and the nature of the reagents, but a period of from 10 minutes to 2 hours will normally suffice.

Step (d)

In this step, the compounds of the invention may be subjected to one or more of various optional steps, including removal of protecting groups, esterification and salification. Protecting groups to be removed will normally be carboxy-protecting or hydroxy-protecting groups. The nature of the removal reaction will depend upon the nature of the group to be removed, as is well-known to those skilled in the art of $\beta$-lactam chemistry.

Where a carboxy-protecting group is to be removed to leave a free carboxy group, it may be removed by reduction. For example, if it is a haloalkyl group, an aralkyl group or a benzhydryl group, it may be removed by contact with a reducing agent. In the case of haloalkyl groups, such as the 2,2-dibromoethyl or 2,2,2-trichloroethyl groups, the preferred reducing agent is a combination of zinc with acetic acid. If the protecting group is an aralkyl group (such as a benzyl or p-nitrobenzyl group) or a benzhydryl group, we prefer that the reduction should be either: catalytic reduction using hydrogen and a suitable catalyst, such as palladium oxide or palladium-on-charcoal; or reduction with an alkali metal sulfide, such as sodium sulfide or potassium sulfide. Whatever the reduction technique, the reduction process is preferably effected in the presence of a solvent, the nature of which is not critical, provided that it has no adverse effect upon the reaction. Suitable solvents include: alcohols, such as methanol or ethanol; ethers, such as tetrahydrofuran or dioxane; fatty acids, such as acetic acid; or a mixture of one or more of these organic solvents with water. The reaction will take place over a wide temperature range, although we generally find it convenient to carry out the reaction at a temperature in the range from $0°$ C. to room temperature. The time required for the reaction will vary, depending upon the nature of the starting materials and reducing agents, but a period of from 5 minutes to 12 hours will normally suffice.

After completion of the reaction, the desired compound, which will then contain a free carboxy group, may be recovered by conventional means from the reaction mixture. For example, a suitable recovery technique comprises: separating off any insoluble precipitate; washing the organic solvent layer with water and, if necessary, drying it; and then distilling off the solvent to give the desired product. This may, if necessary, be further purified by conventional means, for example recrystallization or the various chromatography techniques, such as preparative thin layer chromatography or column chromatography.

Examples of protected hydroxy groups include acyloxy groups, e.g. alkanoyloxy, haloacetoxy and aralkyloxycarbonyloxy groups, and trialkylsilyloxy groups. Where such groups are included to protect a hydroxy group, they may be removed by conventional means, the removal reaction depending upon the nature of the group to be removed.

For example, if the protecting group is a lower (e.g. $C_1$–$C_7$) alkanoyl group, such as an acetyl group, or a haloacetoxy group (such as a trifluoroacetyl or trichloroacetyl group), this may be removed by treating the corresponding compound with a base in the presence of an aqueous solvent. The nature of the solvent is not critical and any such solvent commonly used for hydrolysis reactions may be employed. However, we normally prefer to use water or a mixture of water with an organic solvent, such as an alcohol (e.g. methanol, ethanol or propanol) or an ether (e.g. tetrahydrofuran or dioxane). The nature of the base is also not critical to the process, provided that it does not adversely affect the reaction or any other part of the compound, notably the $\beta$-lactam ring. Preferred bases are alkali metal carbonates, such as sodium carbonate or potassium carbonate. The reaction temperature is not critical and the reaction will take place over a wide range of temperatures, but we normally prefer to employ a temperature of from $0°$ C. to about ambient, in order to reduce or control side reactions. The time required for the reaction will vary, depending upon many factors, including the nature of the starting materials and the reaction temperature, but a period of from 1 to 6 hours will normally suffice.

If the hydroxy-protecting group is an aralkyloxycarbonyl group (such as a benzyloxycarbonyl or p-nitrobenzyloxycarbonyl group), this may be eliminated to restore a free hydroxy group by contacting the compound with a reducing agent. The nature of the reducing agent and the reaction conditions are precisely the same as those employed for removing a carboxy-protecting group where this carboxy-protecting group is an aralkyl group; accordingly, if the compound contains both an aralkyloxycarbonyl group (as hydroxy-protecting group) and an aralkyl group (as carboxy-protecting group), these will normally be removed simultaneously.

Where the compound contains a trialkylsilyloxy group, in which each alkyl group has from 1 to 6 carbon atoms (for example a t-butyldimethylsilyloxy group) as a protected hydroxy group, the protecting group may be eliminated by treating the compound with tetrabutylammonium fluoride. The reaction is preferably effected in the presence of a solvent, the nature of which is not critical, provided that it has no adverse effect upon the reaction; suitable solvents include ethers, such as tetrahydrofuran or dioxane. The reaction is preferably effected at about ambient temperature and the period required for the reaction, which will normally vary depending upon the reagents and the reaction temperature, will normally be from 10 to 18 hours.

After completion of the reactions described above, the desired product may be recovered from the reaction mixture by conventional means. For example, when the reaction is carried out in a buffer solution, the desired product is preferably separated by column chromatography, for example through a column of Diaion (trademark) HP-20AG (a product of Mitsubishi Chemical Industries Co. Limited). Alternatively, if the compound had been obtained by reaction in an organic solvent, the solution is washed with water (if necessary, after transferring the product into solution in a water-immiscible organic solvent), the solution is then, if necessary, dried, and then the solvent is distilled off to give the desired product. This product may, if necessary, be further purified by conventional techniques, for example by recrystallization, reprecipitation or the various chromatography techniques, such as preparative thin layer chromatography or column chromatography.

If desired, any of the reactions discussed above may be carried out employing the ring-opened azetidinone equivalent of the carbapenem or carbapenam compound and then the ring may be closed by a conventional ring-closing Wittig reaction at any appropriate stage, e.g. as described in more detail hereafter as steps (e) and (f).

However, a preferred reaction is as illustrated in the following reaction scheme:

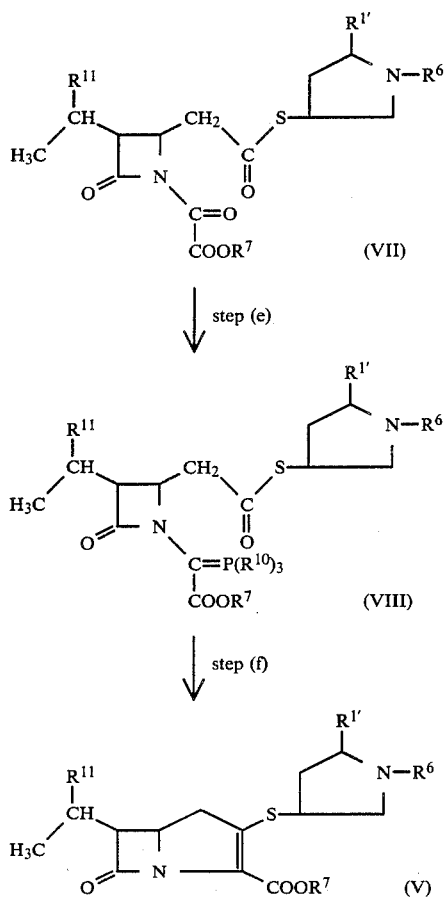

In the above formulae, $R^{1'}$, $R^6$, $R^7$ and $R^{11}$ are as defined above. $R^{10}$ represents an alkoxy group, preferably a $C_1$–$C_6$ alkoxy group, an aralkyloxy group, in which the aryl part is preferably a $C_6$–$C_{10}$ carbocyclic aryl group which is unsubstituted or has one or more substituents, preferably those listed above as possible substituents on aralkyl groups, a dialkylamino group, in which each alkyl part is $C_1$–$C_6$ or a diarylamino group in which each aryl part is a $C_6$–$C_{10}$ carbocyclic aryl group which is unsubstituted or has one or more substituents, preferably those listed above as possible substituents on aralkyl groups.

The compound of formula (VII) used as the starting material in this process may, for example, be prepared as described in copending U.S. patent application Ser. No. 714,373 filed 21 Mar. 1985, the disclosure of which is incorporated herein by reference.

In step (e) of this reaction scheme, the compound of formula (VII) is reacted with a phosphorus compound of formula $P(R^{10})_3$. Particularly preferred phosphorus compounds are the trialkyl phosphites, of which triethyl phosphite, tripropyl phosphite and triisopropyl phosphite are the most preferred. This reaction is preferably effected in the presence of an inert solvent, the nature of which is not critical, provided that it has no adverse effect on the reaction. Suitable solvents include, for example: aliphatic and aromatic hydrocarbons, such as hexane, benzene, toluene or xylene; halogenated hydrocarbons, particularly halogenated aliphatic hydrocarbons, such as chloroform, methylene chloride or 1,2-dichloroethane; esters, such as ethyl acetate; ethers, such as tetrahydrofuran or dioxane; nitriles, such as acetonitrile; and amides, such as dimethylformamide or dimethylacetamide.

The reaction of step (e) is preferably effected with heating, for example at a temperature within the range from 50° to 150° C. The time required for the reaction will vary, depending upon many factors, including the nature of the reagents and the reaction temperature, but a period of from 1 to 10 hours will normally suffice.

At the end of this time, the solvent and other substances are distilled off under reduced pressure, giving the compound of formula (VIII). Depending upon the reaction temperature and the time allowed for the reaction, the compound of formula (VIII) may already have undergone cyclization to convert some or all of that compound into the compound of formula (V). Thus, if the reaction in step (e) was carried out at a temperature within the range from 80° to 150° C. for a period of from 10 hours to 5 days, without isolation of the compound of formula (VIII), the compound (V) is obtained directly. If, however, the compound has not undergone cyclization, then it is preferably heated, e.g. at a temperature within the range from 80° to 150° C. for a period of from 10 hours to 5 days, to give the compound of formula (V) in step (f).

If desired, this compound of formula (V) may be treated in the same way as the compound obtained in step (b), to give the compound of formula (Va) or (I).

The compounds obtained by any of the above methods may, if desired, be salified and/or esterified by conventional means, to give salts and/or esters thereof, examples of such salts and esters being as given hereinabove.

The compounds of the present invention have outstanding antibacterial activity, and combine a lower renal toxicity with high bioavailability. The compounds were tested by the standard agar dilution method and were found to have strong activity against a wide range of pathogenic microorganisms, including both gram-positive bacteria (such as *Staphylococcus aureus* and *Bacillus subtilis*) and gram-negative bacteria (such as *Escherichia coli, Shigella flexneri, Klebsiella pneumoniae, Proteus vulgaris*, Serratia species e.g. *Serratia marcescens*, Enterobacter species e.g. *Enterobacter cloacae, Salmonella enteritidis* and *Morganella morganii*) and are thus useful for the treatment of diseases caused by such microorganisms.

Certain of the compounds of the invention were investigated for their activities against various mircroorganisms. The compounds tested were the isomers of Compounds Nos. 2, 13, 16, 44 and 48 hereinbefore identified. The activities of the test compounds against these microorganisms are shown in the following Table, in terms of their minimal inhibitory concentrations (μg/ml). The specific isomers of these compounds employed in the following tests are those prepared and identified in the subsequent Examples.

TABLE

| Microorganism | Compound No. | | | | |
|---|---|---|---|---|---|
| | 2 | 13 | 16 | 44 | 48 |
| *Staphylococcus aureus* 209P | 0.02 | 0.01 | 0.05 | 0.01 | 0.01 |
| *Staphylococcus aureus* 56 | 0.05 | 0.1 | 0.2 | 0.05 | 0.05 |
| *Escherichia coli* NIHJ | 0.02 | 0.1 | 0.1 | 0.2 | 0.1 |
| *Escherichia coli* 609 | 0.02 | 0.2 | 0.2 | 0.4 | 0.2 |
| *Shigella flexneri* 2a | 0.05 | — | — | — | — |
| *Klebsiella pneumoniae* 806 | 0.05 | 0.1 | 0.2 | 0.2 | 0.2 |
| *Klebsiella* sp. 846 | 0.02 | 0.2 | 0.2 | 0.2 | 0.1 |
| *Proteus vulgaris* | 0.8 | 0.8 | 0.4 | 3.1 | 1.5 |
| *Salmonella enteritidis* G | 0.05 | — | 0.2 | — | 0.2 |
| *Morganella morganii* 1510 | 0.8 | 1.5 | 1.5 | 6.2 | 3.1 |
| *Serratia marcescens* IAM 1184 | 0.05 | 0.4 | 0.4 | 3.1 | 0.2 |

The renal toxicity of the compounds of the invention was also investigated. The test animals used were rabbits of about 3 kg body weight. The compounds under test were employed as aqueous dispersions. The compounds tested were the known antibiotic imipenem and Compound No. 2 (the isomer hereinbefore identified) of the present invention.

The rabbits were divided into two groups, one group (containing 4 rabbits) was given a dose of 75 μg/ml of imipenem by injection into the ear vein. The other group (consisting of 5 rabbits) was similarly given a dose of 150 μg/ml of Compound No. 2.

After one week, the kidneys of the rabbits from each group were excised and examined. In the case of the group given imipenem, degenerative necrosis of the proximal renal tubules in the region of the renal cortex was observed to a substantial extent in all four rabbits. On the other hand, none of the five rabbits in the group given Compound No. 2 showed any sign of tubular necrosis.

These results demonstrate that the compounds of the invention have reduced renal toxicity as compared with known compounds and also have excellent antibacterial activities.

The compounds of the invention may be administered either orally or parenterally for the treatment of diseases in humans and other animals caused by pathogenic microorganisms. The compounds may be formulated into any conventional form for administration. For example, for oral administration, suitable formulations include tablets, granules, capsules, powders and syrups, whilst formulations for parenteral administration include injectible solutions for subcutaneous or intravenous injection.

The dose of the compound of the invention will vary, depending upon the age, body weight and condition of the patient, as well as upon the form and times of administration. However, in general, the adult daily dose is from 200 to 3000 mg of the compound, which may be administered in a single dose or in divided doses.

The preparation of compounds of the invention is further illustrated by the following Examples.

EXAMPLE 1

1(a) p-Nitrobenzyl (5R,6S)-6-[(1(R)-hydroxyethyl]-2-[(2S,4S)-2-carbamoyl-1-(N-p-nitrobenzyloxycarbonylacetimidoyl)pyrrolidin-4-ylthio]-2-carbapenem-3-carboxylate 0.182 ml of diisopropylethylamine and 0.212 ml of diphenylphosphoryl chloride were added, whilst ice-cooling and under a nitrogen stream, to a solution of 303 mg of p-nitrobenzyl (5R,6S)-6-[1(R)-hydroxyethyl]-2-oxocarbapenam-3-carboxylate in 5 ml of acetonitrile, and then the mixture was stirred at the same temperature for 30 minutes. At the end of this time, a solution of 0.182 ml of diisopropylamine and 320 mg of (2S,4S)-1-(N-p-nitrobenzyloxycarbonylacetimidoyl)-2-carbamoyl-4-mercaptopyrrolidine in 10 ml of tetrahydrofuran was added to the mixture, and then the whole mixture was stirred for a further 2 hours. The reaction mixture was diluted with ethyl acetate, washed, in turn, with water and with a saturated aqueous solution of sodium chloride, and dried over anhydrous magnesium sulfate. The solvent was removed by evaporation to give 195 mg of the title compound.

Nuclear Magnetic Resonance Spectrum [90 MHz, DCON(CD$_3$)$_2$] δ ppm: 1.25 (3H, doublet, J=6 Hz); 1.7–2.4 (2H, multiplet); 2.13 & 2.33 (together 3H, each singlet); 2.4–4.8 (12H, multiplet); 5.25 (2H, singlet); 5.35 & 5.47 (2H, AB, J=15 Hz); 7.72 & 8.30 (4H, 2AB, J=8 Hz).

Infrared Absorption Spectrum (KBr) $\nu_{max}$cm$^{-1}$: 3400, 1778, 1680.

1(b) (5R,6S)-6-[1(R)-hydroxyethyl]-2-[(2S,4S)-2-carbamoyl-1-acetimidoylpyrrolidin-4-ylthio]-2-carbapenem-3-carboxylic acid (Compound No. 2)

10 ml of water and 400 mg of 10% w/w palladium-on-charcoal were added to a solution of 193 mg of p-nitrobenzyl (5R,6S)-6-[1(R)-hydroxyethyl]-2-[(2S,4S)-2-carbamoyl-1-(N-p-nitrobenzyloxycarbonylacetimidoyl)pyrrolidin-4-ylthio]-2-carbapenem-3-carboxylate [obtained as described in Example 1(a) above] in 10 ml of tetrahydrofuran, and then the mixture was stirred for 2 hours under a hydrogen atmosphere. At the end of this time, the catalyst was filtered off, the tetrahydrofuran was removed by distillation under reduced pressure, and then the residue was washed with ethyl acetate. The aqueous phase was concentrated by evaporation under reduced pressure to a volume of about 15 ml and it was then subjected to column chromatography through Diaion (trade mark) CHP-20P (Mitsubishi Chemical Industries Ltd), eluted with water, to give 24 mg of the title compound.

Nuclear Magnetic Resonance Spectrum (90 MHz, D$_2$O) δ ppm: 1.10 (3H, doublet, J=6 Hz); 2.06 & 2.18 (together 3H, each singlet); 1.66–2.4 (2H, multiplet); 2.43–4.26 (12H, multiplet).

Ultraviolet Absorption Spectrum (H$_2$O) $\lambda_{max}$nm (ε): 298.5 (8660).

Infrared Absorption Spectrum (KBr) $\nu_{max}$cm$^{-1}$: 3400, 1760, 1690.

EXAMPLE 2

2(a) p-Nitrobenzyl (5R,6S)-6-[1(R)-hydroxyethyl]-2-[(2S,4S)-2-methoxycarbonyl-1-(N-p-nitrobenzyloxycarbonylacetimidoyl)pyrrolidin-4-ylthio]-2-carbapenem-3-carboxylate The procedure described in Example 1(a) was repeated, but using 522 mg of p-nitrobenzyl (5R,6S)-6-[1(R)-hydroxyethyl]-2-oxocarbapenam-3-carboxylate in 30 ml of acetonitrile, 0.313 ml of diisopropylethylamine, 0.367 ml of diphenylphosphoryl chloride, 0.365 ml of diisopropylamine and 800 mg of (2S,4S)-1-(N-p-nitrobenzyloxycarbonylacetimidoyl)-2-methoxycarbonyl-4-mercaptopyrrolidine in 20 ml of acetonitrile, and subjecting the reaction mixture to silica gel column chromatography, to give 780 mg of the title compound.

Nuclear Magnetic Resonance Spectrum [60 MHz, $CD_3COCD_3+(CD_3)_2SO$] δ ppm: 1.26 (3H, doublet, J=6.0 Hz); 1.7–2.4 (1H, multiplet); 2.18 & 2.28 (together, 3H, each singlet); 2.6–4.8 (11H, multiplet); 3.66 (3H, singlet); 5.18 (2H, singlet); 5.30, 5.50 (2H, AB-quartet, J=14 Hz); 7.65, 7.77, 8.22 (8H, 2AB-quartet, J=9.0 Hz).

Infrared Absorption Spectrum (KBr) $\nu_{max}$cm$^{-1}$: 3430, 1775, 1745, 1690.

2(b) (5R,6S)-6-[1(R)-hydroxyethyl]-2-[(2S,4S)-2-methoxycarbonyl-1-acetimidoylpyrrolidin-4-ylthio]-2-carbapenem-3-carboxylic acid (Compound No. 44)

The procedure described in Example 1(b) was repeated, but using 500 mg of the product obtained as described in Example 2(a) in 25 ml of tetrahydrofuran, 25 ml of water and 1 g of 10% w/w palladium-on-charcoal, to give 117 mg of the title compound.

Nuclear Magnetic Resonance Spectrum (270 MHz, $D_2O$) δ ppm: 1.08 (3H, doublet, J=6.6 Hz); 2.05–2.76 (2H, multiplet); 2.11, 2.17 (together 3H, each singlet); 2.98 (2H, doublet, J=9.1 Hz); 3.23 (1H, doublet of doublets, J=2.5, 5.8 Hz); 3.28–4.18 (5H, multiplet); 3.62, 3.64 (together 3H, each singlet); 5.62–5.83 (1H, multiplet).

Infrared Absorption Spectrum (KBr) $\nu_{max}$cm$^{-1}$: 3370, 1770, 1740.

EXAMPLE 3

3(a) p-Nitrobenzyl (5R,6S)-6-[1(R)-hydroxyethyl]-2-[(4S)-2-methoxycarbonyl-1-(p-nitrobenzyloxycarbonyl)pyrrolidin-4-ylthio]-2-carbapenem-3-carboxylate The procedure described in Example 1(a) was repeated, but using 212 mg of p-nitrobenzyl (5R,6S)-6-[1(R)-hydroxyethyl]-2-oxocarbapenam-3-carboxylate in 3 ml of acetonitrile, 0.127 ml of diisopropylethylamine, 0.149 ml of diphenylphosphoryl chloride, 0.127 ml of diisopropylamine and 230 mg of (4S)-1-(p-nitrobenzyloxycarbonyl)-2-methoxycarbonyl-4-mercaptopyrrolidine in 2 ml of acetonitrile, to give 265 mg of the title compound.

Nuclear Magnetic Resonance Spectrum [60 MHz, $DCON(CD_3)_2$] δ ppm: 1.30 (3H, doublet, J=6.6 Hz); 1.7–2.4 (2H, multiplet); 3.1–4.65 (8H, multiplet); 3.39 (2H, doublet, J=9.0 Hz); 5.25 (2H, singlet); 5.28, 5.47 (2H, AB-quartet, J=14.0 Hz); 7.72, 8.16 (8H, 2AB, J=9.0 Hz).

Infrared Absorption Spectrum (KBr) $\nu_{max}$cm$^{-1}$: 3400, 1778, 1750, 1710.

3(b) (5R,6S)-6-[1(R)-hydroxyethyl]-2-[(4S)-2-methoxycarbonylpyrrolidin-4-ylthio]-2-carbapenem-3-carboxylic acid The procedure described in Example 1(b) was repeated, but using 257 mg of the product obtained as described in Example 3(a) in 25 ml of tetrahydrofuran, 25 ml of water and 200 mg of 10% w/w palladium-on-charcoal, to give 36 mg of the title compound.

Nuclear Magnetic Resonance Spectrum (90 MHz, $D_2O$) δ ppm: 1.13 (3H, doublet, J=6.6 Hz); 1.8–2.2 (1H, multiplet); 2.5–3.8 (1H, multiplet); 3.03 (3H, doublet, J=9.0 Hz); 3.1–5.0 (7H, multiplet).

Infrared Absorption Spectrum (KBr) $\nu_{max}$cm$^{-1}$: 3400, 1750, 1592.

Ultraviolet Absorption Spectrum ($H_2O$) $\lambda_{max}$nm (ε): 297 (8519).

3(c) (5R,6S)-6-[1(R)-hydroxyethyl]-2-[(2S,4S)-2-methoxycarbonyl-1-acetimidoylpyrrolidin-4-ylthio]-2-carbapenem-3-carboxylic acid (Compound No. 44)

A solution of 100 mg of the product obtained as described in Example 3(b) in 20 ml of a phosphate buffer solution (pH 7.1) was adjusted to a pH value of 8.5 by the addition of a 1N aqueous solution of sodium hydroxide, whilst ice-cooling. 170 mg of ethyl acetimidate hydrochloride were added to this solution, which was again adjusted to a pH value of 8.5 by the addition of a 1N aqueous solution of sodium hydroxide. The mixture was stirred for 10 minutes whilst ice-cooling, after which it was adjusted to a pH value of 7.0 by the addition of 1N hydrochloric acid. The reaction mixture was passed through a column containing Diaion CHP-20P and eluted with 5% v/v acetone in water. The desired fractions were lyophilised to give 30 mg of the title compound. The nuclear magnetic resonance and infrared spectra of the compound were in good agreement with those of the product of Example 2(b).

EXAMPLE 4

4(a) p-Nitrobenzyl (5R,6S)-6-[1(R)-hydroxyethyl]-2-[(4S)-2-hydroxymethyl-1-(p-nitrobenzyloxycarbonyl)pyrrolidin-4-ylthio]-2-carbapenem-3-carboxylate The procedure described in Example 1(a) was repeated, but using 171 mg of p-nitrobenzyl (5R,6S)-6-[1(R)-hydroxyethyl]-2-oxocarbapenam-3-carboxylate in 3 ml of acetonitrile, 0.102 ml of diisopropylethylamine, 0.120 ml of diphenylphosphoryl chloride, 0.102 ml of diisopropylamine and 320 mg of (4S)-(p-nitrobenzyloxycarbonyl)-2-hydroxymethyl-4-mercaptopyrrolidine in 3 ml of acetonitrile, to give 282 mg of the title compound.

Nuclear Magnetic Resonance Spectrum [60 MHz, $CDCl_3+ DCON(CD_3)_2$] δ ppm: 1.36 (3H, doublet, J=6.0 Hz); 1.8–4.4 (15H, multiplet); 5.18 (2H, singlet); 5.21, 5.42 (2H, AB-quartet, J=14.0 Hz); 7.53, 7.60, 8.12 (8H, 2AB, J=9.0 Hz).

Infrared Absorption Spectrum (KBr) $\nu_{max}$cm$^{-1}$: 3500, 3400, 1772, 1695.

4(b) (5R,6S)-6-[1(R)-hydroxyethyl]-2-[(4S)-2-hydroxymethylpyrrolidin-4-ylthio]-2-carbapenem-3-carboxylic acid The procedure described in Example 1(b) was repeated, but using 265 mg of the product obtained as described in Example 4(a) in 15 ml of tetrahydrofuran, 15 ml of water and 180 mg of 10% w/w palladium-on-charcoal, to give 53 mg of the title compound.

Nuclear Magnetic Resonance Spectrum (90 MHz, D$_2$O) δ ppm: 1.40–1.83 (1H, multiplet); 1.70 (3H, doublet, J=6.6 Hz); 2.23–2.66 (1H, multiplet); 3.03 (2H, doublet, J=9.0 Hz); 3.13–4.23 (9H, multiplet).

Infrared Absorption Spectrum (KBr) $\nu_{max}$cm$^{-1}$: 3370, 1760, 1585.

Ultraviolet Absorption Spectrum (H$_2$O) $\lambda_{max}$nm (ε): 297 (9050).

4(c) p-Nitrobenzyl (5R,6S)-[1(R)-hydroxyethyl]-2-[(4S)-2-acetoxymethyl-1-(p-nitrobenzyloxycarbonyl)pyrrolidin-4-ylthio]-2-carbapenem-3-carboxylate The procedure described in Example 1(a) was repeated, but using 696 mg of p-nitrobenzyl (5R,6S)-6-[1(R)-hydroxyethyl]-2-oxocarbapenam-3-carboxylate in 15 ml of acetonitrile, 0.418 ml of diisopropylethylamine, 0.489 ml of diphenylphosphoryl chloride, 0.418 ml of diisopropylamine and 780 mg of (4S)-1-(p-nitrobenzyloxycarbonyl)-2-acetoxymethyl-4-mercaptopyrrolidine in 15 ml of acetonitrile, to give 1.2 g of the title compound.

Nuclear Magnetic Resonance Spectrum (60 MHz, CDCl$_3$) δ ppm: 1.34 (3H, doublet, J=6.0 Hz); 2.03 (3H, singlet); 1.7–2.8 (2H, multiplet); 3.18 (2H, doublet, J=8.0 Hz); 3.35–4.40 (8H, multiplet); 5.16 (2H, singlet); 5.18, 5.40 (2H, AB-quartet, J=14.0 Hz); 7.47, 7.53, 8.12 (8H, 2AB, J=9.0 Hz).

Infrared Absorption Spectrum (KBr) $\nu_{max}$cm$^{-1}$: 3420, 1770, 1735, 1710.

4(d) p-Nitrobenzyl (5R,6S)-[1(R)-hydroxyethyl]-2-[(4S)-2-acetoxymethyl-1-(p-nitrobenzyloxycarbonyl)pyrrolidin-4-ylthio]-2-carbapenem-3-carboxylate 5 g of the product obtained as described in Example 4(a), 10 ml of acetic anhydride and 0.5 ml of pyridine were mixed at room temperature for 3 hours. Water was added to the reaction mixture, which was then extracted with ethyl acetate, washed with water and dried. The solvent was removed by evaporation under reduced pressure to leave a residue, which was then purified by silica gel column chromatography, to give 2.5 g of the title compound.

The nuclear magnetic resonance and infrared spectra were in good agreement with those of the product obtained as described in Example 4(c).

4(e) (5R,6S)-[1(R)-hydroxyethyl]-2-acetoxymethylpyrrolidin-4-ylthio]-2-carbapenem-3-carboxylic acid The procedure described in Example 1(b) was repeated, but using all of the product obtained in Example 4(c) in 60 ml of tetrahydrofuran, 40 ml of water and 1.8 g of 10% w/w palladium-on-charcoal, to give 150 mg of the title compound.

Nuclear Magnetic Resonance Spectrum (90 MHz, D$_2$O) δ ppm: 1.09 (3H, doublet, J=6.6 Hz); 1.4–2.1 (1H, multiplet); 2.00 (3H, singlet); 2.2–2.8 (1H, multiplet); 3.00 (2H, doublet, J=9.0 Hz); 3.1–4.6 (9H, multiplet).

Infrared Absorption Spectrum (KBr) $\nu_{max}$cm$^{-1}$: 3420, 1770, 1745, 1590.

Ultraviolet Absorption Spectrum (H$_2$O) $\lambda_{max}$nm (ε): 297 (9027).

4(f) (5R,6S)-6-[1(R)-hydroxyethyl]-2-[(4S)-2-acetoxymethyl-1-acetimidoylpyrrolidin-4-ylthio]-2-carbapenem-3-carboxylic acid (Compound No. 48)

The procedure described in Example 3(c) was repeated, but using 100 mg of the product obtained as described in Example 4(e) and 169 mg of ethyl acetimidate hydrochloride, to give 27 mg of the title compound.

Nuclear Magnetic Resonance Spectrum (90 MHz, D$_2$O) δ ppm: 1.07 (3H, doublet, J=6.6 Hz); 1.97 (3H, singlet); 1.85, 2.03 (together 3H, each singlet); 1.73–1.83 (4H, multiplet); 3.03 (2H, doublet, J=9.0 Hz); 3.13–4.43 (7H, multiplet).

Infrared Absorption Spectrum (KBr) $\nu_{max}$cm$^{-1}$: 3380, 1770, 1745, 1670, 1590.

Ultraviolet Absorption Spectrum (H$_2$O) $\lambda_{max}$nm (ε): 299 (5612).

EXAMPLE 5

5(a) p-Nitrobenzyl (5R,6S)-6-[1(R)-hydroxyethyl]-2-[(2S,4S)-2-N-methylcarbamoyl-1-(N-p-nitrobenzyloxycarbonylacetimidoyl)pyrrolidin-4-ylthio]-2-carbapenem-3-carboxylate The procedure described in Example 1(a) was repeated, but using 522 mg of p-nitrobenzyl (5R,6S)-6-[1(R)-hydroxyethyl]-2-oxocarbapenam-3-carboxylate in 20 ml of acetonitrile, 0.313 ml of diisopropylethylamine, 0.367 ml of diphenylphosphoryl chloride, 0.365 ml of diisopropylamine and 798 mg of (2S,4S)-1-(N-p-nitrobenzyloxycarbonylacetimidoyl)-2-N-methylcarbamoyl-4-mercaptopyrrolidine in 40 ml of acetonitrile, to give 195 mg of the title compound were obtained.

Nuclear Magnetic Resonance Spectrum [60 MHz, (CD$_3$)$_2$SO] δ ppm: 1.30 (3H, doublet, J=6 Hz); 1.5–2.5 (2H, multiplet); 2.05, 2.25 (together 3H, each singlet); 2.56 (3H, doublet, J=4.0 Hz); 3.0–4.7 (10H, multiplet); 5.13 (2H, singlet); 5.26, 5.41 (2H, AB-quartet, J=14.0 Hz); 7.58, 7.68, 8.17 (8H, 2AB-quartet, J=9.0 Hz).

Infrared Absorption Spectrum (KBr) $\nu_{max}$cm$^{-1}$: 3300, 1775, 1660.

5(b) (5R,6S)-6-[1(R)-hydroxyethyl]-2-[(2S,4S)-2-N-methylcarbamoyl-1-acetimidoylpyrrolidin-4-ylthio]-2-carbapenem-3-carboxylic acid (Compound No. 13)

The procedure described in Example 1(b) was repeated, but using 500 mg of the product obtained as described in Example 5(a) in 25 ml of tetrahydrofuran, 25 ml of water and 1 g of 10% w/w palladium-on-charcoal, and making the volume of the aqueous layer before subjecting it to column chromatography to about 40 ml, to give 186 mg of the title compound.

Nuclear Magnetic Resonance Spectrum (270 MHz, D$_2$O) δppm: 1.08 (3H, doublet, J=6.2 Hz); 2.0–2.2 (1H, multiplet); 2.03, 2.18 (together 3H, each singlet); 2.58, 2.59 (together 3H, each singlet); 2.66–2.78 (1H, multiplet); 2.99 (2H, doublet, J=9.1 Hz); 3.22 (1H, doublet of doublets, J=2.5 & 5.9 Hz); 3.37-3.62 (1H multiplet); 3.79-4.10 (4H, multiplet); 4.43-4.63 (1H, multiplet).

Infrared Absorption Spectrum (KBr) $\nu_{max}$cm$^{-1}$: 3250, 1765, 1670, 1615, 1585.

EXAMPLE 6

6(a)
p-Nitrobenzyl(5R,6S)-6-[1(R)-hydroxyethyl]-2-[(2S,4S)-2-N,N-dimethylcarbamoyl-1-(N-p-nitrobenzyloxycarbonylacetimidoyl)pyrrolidin-4-ylthio]-2-carbapenem-3-carboxylate The procedure described in Example 1(a) was repeated, but using 522 mg of p-nitrobenzyl (5R,6S)-6-[1(R)-hydroxyethyl]-2-oxocarbapenam-3-carboxylate in 20 ml of acetonitrile, 313 ml of diisopropylethylamine, 0.367 ml of diphenylphosphoryl chloride, 365 ml of diisopropylamine and 799 mg of (2S,4S)-1-(N-p-nitrobenzyloxycarbonylacetimidoyl)-2-N,N-dimethylcarbamoyl-4-mercaptopyrrolidine in 3 ml of acetonitrile, and subjecting the reaction product to silica gel column chromatography, to give 967 mg of the title compound.

Nuclear Magnetic Resonance Spectrum (60 MHz, CD$_3$COCD$_3$) δ ppm: 1.28 (3H, doublet, J=6.0 Hz); 1.5-2.5 (2H, multiplet); 2.04, 2.26 (together 3H, each singlet); 2.5-4.5 (9H, multiplet); 2.85 (3H, singlet); 3.04 (3H, singlet); 4.97 (1H, triplet, J=8.0 Hz); 5.15 (2H, singlet); 5.28, 5.47 (2H, AB-quartet, J=14.0 Hz); 7.72, 7.68, 8.17 (8H, 2AB-quartet, J=9.0 Hz).

Infrared Absorption Spectrum (KBr) $\nu_{max}$cm$^{-1}$: 3400, 1775, 1655.

6(b)
(5R,6S)-[1(R)-hydroxyethyl]-2-[(2S,4S)-2-N,N-dimethylcarbamoyl-1-acetimidoylpyrrolidin-4-ylthio]-2-carbapenum-3-carboxylic acid (Compound No. 16)

The procedure described in Example 1(b) was repeated, but using 800 mg of the product obtained as described in Example 6(a) in 40 ml of tetrahydrofuran. 40 ml of water and 1.6 g of 10% w/w palladium-on-charcoal, and making the volume of the aqueous layer to about 60 ml, to give 184 mg of the title compound.

Nuclear Magnetic Resonance Spectrum (270 MHz, D$_2$O) δ ppm: 1.08 (3H, doublet, J=6.6 Hz); 1.7-2.1 (1H, multiplet); 1.93, 2.18 (together 3H, each singlet); 2.7-3.1 (1H, multiplet); 2.77, 2.79 (together 3H, each singlet); 2.89, 2.93 (together 3H, each singlet); 3.01 (2H, doublet-like, J=9.5 Hz); 3.22 (1H, doublet of doublets, J=2.5 & 5.9 Hz); 3.32-3.53 (1H, multiplet); 3.72-4.16 (4H, multiplet); 4.78-5.07 (1H, multiplet). Infrared Absorption Spectrum (KBr) $\nu_{max}$cm$^{-1}$: 3400, 1765, 1640, 1585.

EXAMPLE 7

7(a)
(3S,4R)-4-{[(2S,4S)-2-Carbamoyl-1-[N-(p-nitrobenzyloxycarbonyl)acetimidoyl]pyrrolidin-4-ylthio]carbonylmethyl}-3-[1(R)-(p-nitrobenzyloxycarbonyloxy)ethyl]-1-[1-(p-nitrobenzyloxycarbonyl)-1-triisopropoxyphosphoranylidenemethyl]-2-azetidinone 454 mg (0.5 mmole) of (3S,4R)-4-{[(2S,4S)-2-carbamoyl-1-[N-(p-nitrobenzyloxycarbonyl)acetimidoyl]pyrrolidin-4-ylthio]carbonylmethyl}-3-[1(R)-(p-nitrobenzyloxycarbonyloxy)ethyl]-1-(p-nitrobenzyloxyalyl)-2-azetidinone and 520 mg (2.5 mmole) of triisopropyl phosphite were dissolved in 10 ml of toluene. The solution was heated in a stream of a nitrogen gas at 90° C. for 2 hours. The solvent was then distilled off under reduced pressure. The residue was subjected to chromatography using a Lobar column eluted with a 30:10:1 by volume mixture of ethyl acetate, chloroform and methanol, to afford 330 mg (yield 60%) of the title product as an oily substance.

7(b)
p-Nitrobenzyl(5R,6S)-2-{(2S,4S)-2-carbamoyl-1-[N-(p-nitrobenzyloxycarbonyl)acetimidoyl]pyrrolidin-4-ylthio}-6-[1(R)-(p-nitrobenzyloxycarbonyloxy)ethyl]carbapen-2-em-3-carboxylate A mixture of 300 mg of (3S,4R)-4-{[(2S,4S)-2-carbamoyl-1-[N-(p-nitrobenzyloxycarbonyl)acetimidoyl]pyrrolidin-4ylthio]carbonylmethyl}-3-[1(R)-(p-nitrobenzyloxycarbonyloxy)ethyl]-1-[1-(p-nitrobenzyloxycarbonyl)-1-triisopropoxyphosphoranylidenemethyl]-2-azetidinone [prepared as described in Example 7(a)] and 10 mg of hydroquinone in 30 ml of toluene was heated at 110° C. under a stream of a nitrogen gas for 24 hours. The toluene was then distilled off under reduced pressure and the residue was subjected to liquid chromatography using a Lobar column A eluted with a 10:30:1 by volume mixture of chloroform, ethyl acetate and methanol, to afford 120 mg of the title product.

7(c)
(5R,6S)-2-[(2S,4S)-2-Carbamoyl-1-acetimidoylpyrrolidin-4ylthio]-6-[1(R)-hydroxyethyl]carbapen-2-em-3-carboxylic acid (Compound No. 2)

500 mg of p-nitrobenzyl (5R,6S)-2-{(2S,4S)-2-carbamoyl-1-[N-(p-nitrobenzyloxycarbonyl)acetimidoyl]pyrrolidin-3ylthio}-6-[1(R)-(p-nitrobenzyloxycarbonyloxy)ethyl]carbapen-2-em-3-carboxylate [prepared as described in Example 7(b)] were dissolved in a mixture of 25 ml of tetrahydrofuran and 25 ml of a 0.1M phosphate buffer solution (pH 7.1). To the solution was added 1.4 g of a 10% w/w palladium-on-charcoal catalyst and the mixture was stirred under a stream of hydrogen gas at atmospheric pressure for 70 minutes. At the end of this time, the catalyst was filtered off and 15 ml of the above buffer solution were added to the filtrate. The mixture was washed with ethyl acetate. The aqueous layer was separated and concentrated to above one half of its original volume by evaporation at room temperature under reduced pressure. The concentrate was subjected to column chromatography through 20 ml of Diaion CHP-20P resin. Fractions eluted with water were collected and lyophilized, to afford 120 mg of the title product as a white powder.

The nuclear magnetic resonance and infrared spectra of the product were in good agreement with those of the product of Example 1(b).

EXAMPLE 8

8(a) p-Nitrobenzyl (5R,6S)-6-[1(R)-trimethylsilyloxyethyl]-2-{(2S,4S)-2-carbamoyl-1-[N-(p-nitrobenzyloxycarbonyl)acetimidoyl]pyrrolidin-4-ylthio}-2-carbapenem-3-carboxylate 454 mg (0.5 mmole) of (3S,4R)-3-[1(R)-(trimethylsilyloxy)ethyl]-4-[{(2S,4S)-2carbamoyl-1-[N-(p-nitrobenzyloxycarbonyl)acetimidoyl]pyrrolidin-4-ylthio}carbonylmethyl]-1-(p-nitrobenzyloxyoxalyl)-2-azetidinone, 10 mg of hydroquinone and 1 ml of triethyl phosphite were dissolved in 80 ml of xylene. The solution was heated under a stream of nitrogen gas at 110° C. for 24 hours. The solvent was then distilled off under reduced pressure. The residue was subjected to chromatography using a Lobar column eluted with a 2:1 by volume mixture of ethyl acetate and benzene, to afford 200 mg of the title compound as an oily substance.

8(b)

(5R,6S)-6-[1(R)-Hydroxyethyl]-2-[(2S,4S)-2-carbamoyl-1-acetimidoylpyrrolidin-4-ylthio]carbapen-2-em-3-carboxylic acid (Compound No. 2)

To a solution of 200 mg of the product prepared as described in Example 8(a) in 2 ml of acetonitrile were added a solution of 40 mg of potassium fluoride in 1 ml of water and 0.1 ml of acetic acid. The mixture was stirred at room temperature for 1 hour, after which it was extracted with ethyl acetate. The extract was washed with water and dried over anhydrous magnesium sulfate. The solvent was distilled off under reduced pressure to leave an oil, which was then dissolved in a mixture of 10 ml of tetrahydrofuran and 10 ml of a 0.1M phosphate buffer solution. The solution was then treated in the same manner as in Example 7(c) to give 60 mg of the title compound, whose physical characteristics were in good agreement with those of the product of Example 1(b).

We claim:

1. A compound of formula (I):

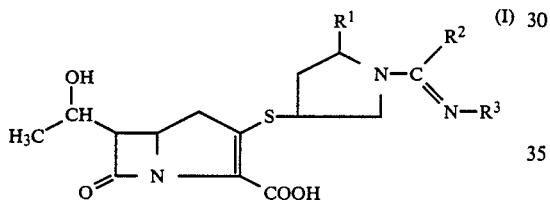

in which:
$R^1$ is a carbamoyl group;
$R^2$ is selected from the group consisting of hydrogen and methyl, ethyl and methoxymethyl groups; and
$R^3$ is a hydrogen atom;
and pharmaceutically acceptable salts and esters thereof.

2. The compound as claimed in claim 1, which is (5R,6S)-6-[1(R)-hydroxyethyl]-2-(2-carbamoyl-1-acetimidoylpyrrolidin-4-ylthio)-2-carbapenem-3-carboxylic acid and pharmaceutically acceptable salts and esters thereof.

3. The compound as claimed in claim 1, which is (5R,6S)-6-[1(R)-hydroxyethyl]-2-[2-carbamoyl-1-(α-methoxyacetimidoyl)pyrrolidin-4-ylthio]-2carbapenem-3-carboxylic acid and pharmaceutically acceptable salts and esters thereof.

4. A pharmaceutical composition for the treatment of bacterial infections, comprising an antibiotically effective amount of an antibiotic compound in admixture with a pharmaceutically acceptable carrier or diluent, wherein the antibiotic compound is selected from the group consisting of compounds of formula (I):

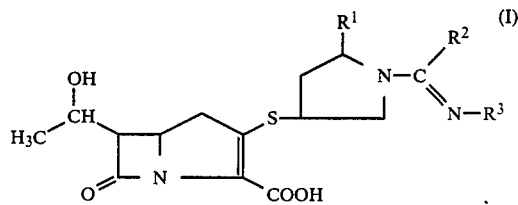

in which:
$R^1$ is a carbamoyl group;
$R^2$ is selected from the group consisting of hydrogen and methyl, ethyl and methoxymethyl groups; and
$R^3$ is a hydrogen atom;
and pharmaceutically acceptable salts and esters thereof.

5. A pharmaceutical composition as claimed in claim 4, wherein said antibiotic compound is selected from the group consisting of:
(5R,6S)-6-[1(R)-hydroxyethyl]-2-(2-carbamoyl-1-acetimidoylpyrrolidin-4-ylthio)-2-carbapenem-3-carboxylic acid;
(5R,6S)-6-[1(R)-hydroxyethyl]-2-[2-carbamoyl-1-(α-methoxyacetimidoyl)pyrrolidin-4ylthio]-2-carbapenem-3-carboxylic acid;
and pharmaceutically acceptable salts and esters thereof.

* * * * *